United States Patent
Dye et al.

(10) Patent No.: US 6,946,019 B2
(45) Date of Patent: Sep. 20, 2005

(54) MENISCUS MEMBRANES FOR SEPARATIONS

(75) Inventors: Robert C. Dye, Irvine, CA (US); Betty Jorgensen, Jemez Springs, NM (US); David R. Pesiri, Aliso Viejo, CA (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 10/766,257

(22) Filed: Jan. 27, 2004

(65) Prior Publication Data

US 2004/0187558 A1 Sep. 30, 2004

Related U.S. Application Data

(62) Division of application No. 09/826,484, filed on Apr. 4, 2001, now Pat. No. 6,681,648.

(51) Int. Cl.⁷ .......................... B01D 61/00; B01D 71/06
(52) U.S. Cl. .............................................. 96/4; 137/79
(58) Field of Search .................... 96/FOR 108, 4; 137/79; 95/14, 43

(56) References Cited

U.S. PATENT DOCUMENTS

| | | | | | |
|---|---|---|---|---|---|
| 1,988,956 A | * | 1/1935 | Newell | ...................... | 137/79 X |
| 2,476,400 A | * | 7/1949 | Berkholder | ............... | 137/79 X |
| 3,455,316 A | * | 7/1969 | Rogers | ...................... | 137/79 X |
| 4,933,083 A | * | 6/1990 | Jones, Jr. | ..................... | 210/490 |
| 5,320,127 A | * | 6/1994 | Yanagihara et al. | ...... | 137/79 X |
| 6,129,105 A | * | 10/2000 | Hec et al. | ................. | 137/79 X |
| 6,464,425 B1 | * | 10/2002 | Closkey | ....................... | 96/4 X |

* cited by examiner

Primary Examiner—Thomas P. Noland
(74) Attorney, Agent, or Firm—Bruce H. Cottrell

(57) ABSTRACT

Gas separation membranes, especially meniscus-shaped membranes for gas separations are disclosed together with the use of such meniscus-shaped membranes for applications such as thermal gas valves, pre-concentration of a gas stream, and selective pre-screening of a gas stream. In addition, a rapid screening system for simultaneously screening polymer materials for effectiveness in gas separation is provided.

2 Claims, 6 Drawing Sheets

MENISCUS MEMBRANES FOR SEPARATIONS

This application is a divisional of Ser. No. 09/826,484, filed Apr. 4, 2001 now U.S. Pat. No. 6,681,648 by Dye et al.

FEDERALLY SPONSORED RESEARCH OR DEVELOPMENT

This invention was made with government support under Contract No. W-7405-ENG-36 awarded by the U.S. Department of Energy. The government has certain rights in the invention.

TECHNICAL FIELD OF THE INVENTION

The present invention relates to separation membranes, more particularly to gas separation membranes, and especially to meniscus-shaped membranes for gas separations as well as the use of such meniscus-shaped membranes for applications such as thermal gas valves, pre-concentration of a gas stream, and selective pre-screening of a gas stream.

BACKGROUND OF THE INVENTION

The last decade has seen a dramatic increase in the use of polymer membranes as an effective, economical and flexible tool for many gas separations. The processability, gas solubility, and selectivity of several classes of polymers (such as polyimides, polysulfones, polyesters and the like) have led to their use in a number of successful gas separation applications. A drawback to the use of polymer membranes for gas separation can be their low permeability. In most instances, the success of a given membrane rests on achieving adequate fluxes.

The commercial use of polymer membranes for air separation, the recovery of hydrogen from mixtures of nitrogen, carbon monoxide and methane, and the removal of carbon dioxide from natural gas has been reported. In each of these applications, high fluxes and excellent selectivities have relied upon glassy polymer membranes which rely on gas size differences for separation of species. Yet, this technology has focused on optimizing separation materials for near ambient conditions. The development of polymeric materials that achieve good combinations of high selectivity, high permeability, mechanical stability and processability at temperatures above about 25° C. and pressures above about 10 bar has been needed.

Separation of carbon dioxide ($CO_2$) from mixed gas streams is of major industrial interest. Continued improvements in such separations are sought. Commercially viable membrane-based approaches to industrial $CO_2$ separations require reduction in costly drops in operating temperatures and pressures while maintaining high fluxes. The need for higher flux $CO_2$ separation approaches remains.

Other research efforts have been directed to the development of polymer membranes that operate at elevated temperatures and pressures.

Through the efforts of the present inventors, a polymer membrane design has now been achieved which can operate under high fluxes. Such a polymer membrane design involves a meniscus-shaped polymer membrane within one or more small pore or opening. That polymer membrane design allows for a number of varying applications described herein.

It is an object of this invention to provide a polymer membrane capable of operation under high fluxes.

It is another object of this invention to provide a meniscus-shaped polymer membrane within one or more small pore or opening, the meniscus-shaped polymer membrane contained substantially completely within such small pores or openings.

Still another object of the present invention is a process for rapidly screening polymers for membranes in non-ambient gas separations by use of such a meniscus-shaped polymer membrane.

Still another object of the present invention is the use of a meniscus-shaped polymer membrane as a selective pre-screen, e.g., for a sensor system including a sensor element where the meniscus-shaped polymer membrane can serve to screen out molecules that would contaminate the sensor element.

Still another object of the present invention is the use of a meniscus-shaped polymer as a pressure/temperature sensor element.

Still another object of the present invention is the use of a meniscus-shaped polymer as a pre-concentrator for a gas stream prior to entry into, e.g., a mass spectrometer.

Still another object of the present invention is the use of a meniscus-shaped polymer as a temperature controlled valve in a gas separation system.

SUMMARY OF THE INVENTION

To achieve the foregoing and other objects, and in accordance with the purposes of the present invention, as embodied and broadly described herein, provides a process for simultaneously screening a multiplicity of polymer materials for comparative effectiveness in gas separation, the process including preparing an array of individual testing ports on a substrate, each individual port including a pore passing through said substrate, a gas inlet to said pore at a first location of said substrate and a gas outlet from said pore at a second location of said substrate, placing said multiplicity of polymer materials, each within a pore of at least one individual port in an amount sufficient to form a meniscus-shaped polymer membrane within said pore, passing a pre-selected gas flow to said gas inlet, analyzing gas flow from said gas outlet, and, comparing gas separation properties for said multiplicity of polymer materials.

The present invention further provides a screening system for simultaneously screening polymer materials for effectiveness in gas separation including a substrate containing an array of individual ports, each port including a pore passing through said substrate, a gas inlet to said pore at a first location of said substrate and a gas outlet from said pore at a second location of said substrate, a meniscus-shaped polymer membrane situated within said pore with each meniscus-shaped polymer membrane formed of a pre-selected polymer material, and, a gas analyzer controllable attached to said outlet gas flows.

The present invention further provides the improvement in a gas separation process using a solid polymer membrane as a gas separator, wherein said solid polymer membrane is selected through the above-described screening process.

The present invention further provides a gas separation module including a substrate containing at least one opening therein, and, a polymer material contained within the opening of said substrate, said polymer material characterized as forming a meniscus-shaped separator within said opening.

The present invention further provides a temperature gas valve including a gas separation module including a substrate containing at least one opening therein and a polymer material contained within the opening of said substrate, said polymer material characterized as forming a meniscus-shaped separator within said opening, said temperature gas valve characterized as preventing a pre-selected gas to pass through said polymer material at a first temperature, but allowing said pre-selected gas to pass through said polymer material at a second temperature.

The present invention further provides an improvement in a detector including a sensing element responsive to the presence of a pre-selected species, said sensing element characterized as subject to deactivation in the presence of selected volatile organic materials, the improvement being location of a polymer membrane between said sensing element and any ambient atmosphere, said polymer membrane capable of allowing said pre-selected species to pass therethrough to said sensing element and said polymer membrane capable of preventing sufficient selected volatile organic materials to pass therethrough to said sensing element whereby said sensing element is deactivated.

DETAILED DESCRIPTION

The present invention is concerned with solid polymer membranes for gas separation. Additionally, the present invention is concerned with a system and process for determining and optimizing the operating temperature ranges of solid polymer membranes for gas separation.

By the term "solid" is meant that the membranes are substantially non-porous and do not contain a liquid element as would be the case in a liquid supported membrane system.

Figure 1:
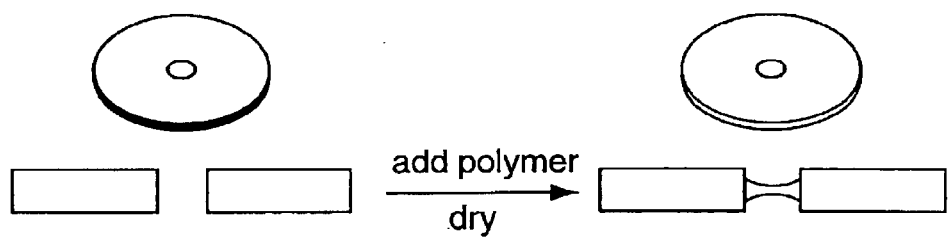
FIG. 1 shows a schematic drawing illustrating preparation of a meniscus-shaped membrane within a small pore or opening in accordance with the present invention.

The present invention involves a gas separation membrane formed by the self-assembly of a solid polymer membrane or film into a thin meniscus that spans a small hole, pore or opening. The solid polymer membrane is formed by a process driven by capillary forces, viscosity, and surface adhesion effects. The result is a thin polymeric membrane or film that is strongly bound to the edges of a hole, pore or opening in a substrate. The seal between the solid polymer membrane and the substrate material defining the pore, hole or opening can be gas tight at pressures in excess of 100 pounds per square inch (psig). An important feature of the resulting solid polymer membrane is its non-uniform thickness throughout the span of the film. The meniscus that forms when the polymer dries in the hole is characterized by a thick structure at the point of attachment to the support material (the sides of the hole) and a minimum thickness at the center of the membrane (FIG. 1). The result is a solid polymer membrane that self-assembles into a concave "lens."

Figure 2:
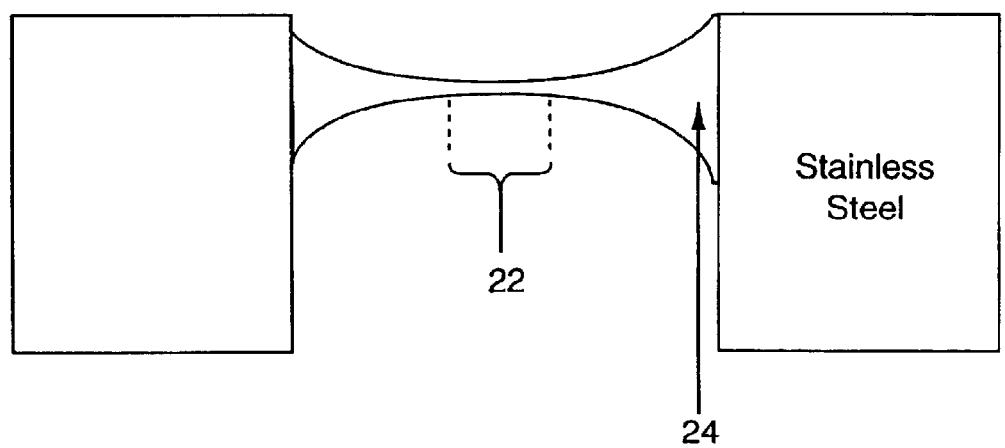
FIG. 2 shows a sideview of the meniscus-shaped membrane in accordance with the present invention.

The shape of the membrane resulting from this invention leads to separation properties well suited to several applications. The desirability of high fluxes in gas separation makes thin membranes attractive. The typical problem with thin polymer films is their fragility, even in composite structures. In capitalizing on the natural formation of a structurally optimized meniscus, this process yields membranes that are both thin and strong. FIG. 2 shows the reduced thickness 22 at the center of the film acting to enhance flux while maintaining a large contact area 24 with the metal support to improve strength. The inherent strength of the concave arch structure can surpass the strength of flat sheet membrane geometry.

In general, the meniscus membrane can range in thickness of from about 5 microns to about 100 microns with greater thickness at the edges of from about 7 microns to about 100 microns, tapering to as thin as from about 5 microns to about 50 microns at the center. The size of the meniscus membrane is limited only by the particular physical properties of the polymer material and the size of the hole, pore or opening. Generally, the size of any individual hole, pore or opening can be from about 0.003 inches in diameter to about 0.25 inches in diameter, preferably from about 0.03 inches in diameter to about 0.1 inches in diameter. A polymer meniscus membrane formed with a concave structure that affords a thin membrane thickness in the center will maximize permeability.

In one embodiment of the present invention, the substrate containing the holes, pores or openings can be a porous metal or porous ceramic substrate. An example of a suitable substrate is a commercially available ceramic substrate element made from silicon carbide. Another preferred substrate can be formed of a porous metal medium such as sintered porous stainless steel. Such a porous metal medium is available from Pall Corporation of East Hills, N.Y. under the trade names PSS (a sintered stainless steel powder metal medium), PMM (a porous sintered metal membrane including metal particles sintered to a foraminate support), PMF (a porous sintered fiber metal medium), Rigimesh (a sintered woven wire mesh medium), Supramesh (stainless steel powder sintered to a Rigimesh support), PMF II (a porous sintered fiber metal medium), and combinations of more than one of these materials. A sintered metal medium for use in the present invention may be formed from any of a variety of metal materials including alloys of various metals such as nickel, chromium, copper, molybdenum, tungsten, zinc, tin, gold, silver, platinum, aluminum, cobalt, iron, and magnesium, as well as combinations of metals and metal alloys, including boron-containing alloys. Brass, bronze, and nickel/chromium alloys, such as stainless steels, the Hastelloys, the Monels and the Inconels, as well as a 50 weight percent nickel/50 weight percent chromium alloy, may also be used. Examples of other suitable high temperature substrates include those formed of glass fibers.

In the present invention, the solid polymer material is characterized as being substantially within the pores, holes or openings of the substrate. That is, the solid polymer material forming the meniscus-shaped membrane does not extend outside of the pores, holes or openings of the substrates to the outer surfaces of the substrate. This allows minimization of polymer material needed. In some instances, it may be desirable to apply a release material such as a polytetrafluoroethylene (PTFE) to selected surfaces of the substrate to prevent the polymer material from adhering at those locations. In some instances, a bonding agent such as a suitable silane material (e.g., a silane coupling agent such as, an alkyl siloxane or phenyl triethoxysilane) can be used to promote greater adhesion of the polymer material at certain locations.

In a process of preparation of such a meniscus membrane, a selected amount of polymer material can be placed into the pore, opening or hole in the substrate and the combination heated above the melting point of the polymer to allow it to form the meniscus-shaped membrane. Optionally, the selected amount of polymer material in conjunction with a suitable solvent for such material can be placed into the pore, opening or hole and the solvent evaporated from the system such that the polymer forms the meniscus-shaped membrane. In another embodiment, a substrate containing the openings, holes or pores can be dipped into an amount of the polymer material where the polymer material can penetrate the openings, holes or pores. Thereafter, the surfaces of the substrate can be wiped to remove excess polymer material. Selected regions can be pre-treated with a release material and/or bonding agent as well.

Figure 3:
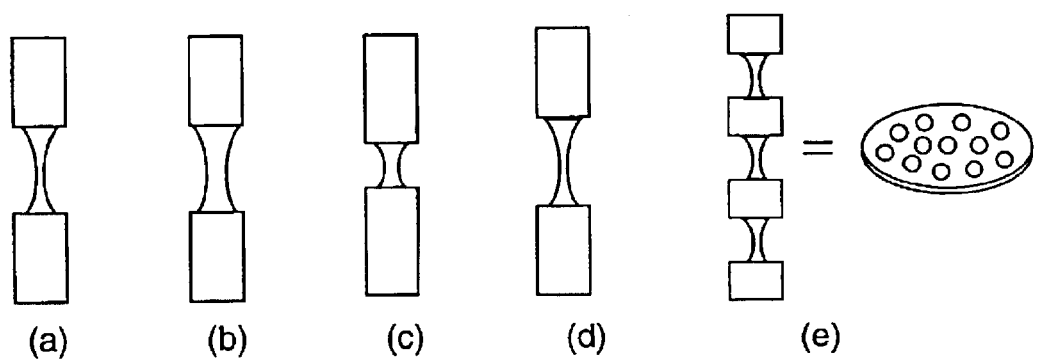
FIGS. 3(a)–(e) show embodiments of meniscus-shaped membranes in accordance with the present invention.

The simplicity of this meniscus membrane design is desirable as well. One sizeable hurdle to adopting polymer membranes in commercial devices is the difficulty in producing robust, inexpensive modules. The approach of the present invention can allow sealing and fixturing using a metal surface (the supporting disk) eliminating the need to seal the polymer in the membrane module. From a research standpoint this meniscus membrane design has several advantages. The ability to screen polymers rapidly by making a gas tight seal can expedite membrane testing. The versatility of the meniscus membrane structure is also an advantage. Control over the size and shape of the hole, pore or opening, the quantity of polymer loaded, and the chemical composition of the polymer can be useful in optimizing gas separation performance for particular applications. The ability to optimize the polymer performance and adjust the hole shape for increased strength is shown below. From FIG. 3(a) to FIG. 3(b) is shown an increase in polymer loading such that the mensicus-shaped membrane has a greater thickness. From FIG. 3(a) to FIG. 3(c) is shown a reduced hole size. The polymer chemistry of the mensicus-shaped membrane is shown represented by the darker membrane of FIG. 3(d). An increase in gas flux rate can be obtained with the multiple pore/openings of the substrate in FIG. 3(e).

Figure 4:
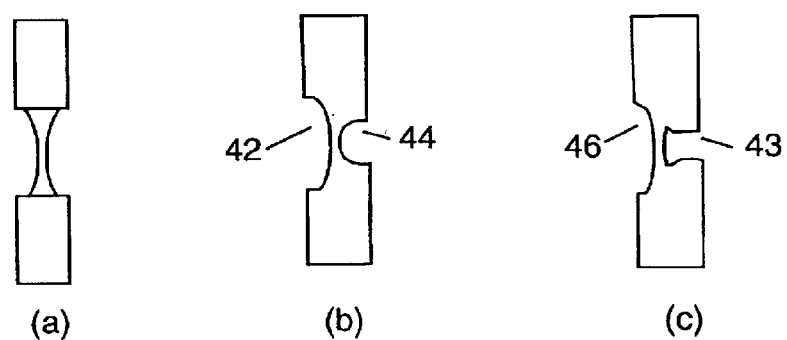
FIGS. 4(a)–(c) show additional embodiments of meniscus-shaped membranes with alternative pore or opening structures in accordance with the present invention.

By changing the shape of the hole or opening, particularly when such a hole or opening is within a supporting substrate (e.g., a metal or ceramic disk), the strength of the surface bonding between the meniscus shaped membrane and the surface of the substrate may be altered. Examples of such altered shapes of holes/openings are those shown in FIGS. 4(a)–(c) where FIG. 4(a) shows a typical shaped opening while FIG. 4(b) shows tapered openings 42 and 44, and FIG. 4(c) shows other tapered openings 46 and 48. Other modifications to the shapes of the holes or openings will be readily apparent to those skilled in the art.

In the present invention, the meniscus membranes are operated at high temperature ranges generally in excess of about 100° C., and often more preferably at high temperature ranges generally in excess of about 200° C. By use of such temperature ranges, the meniscus membranes can have different selectivity than found at more traditional ambient range temperatures.

Figure 5:
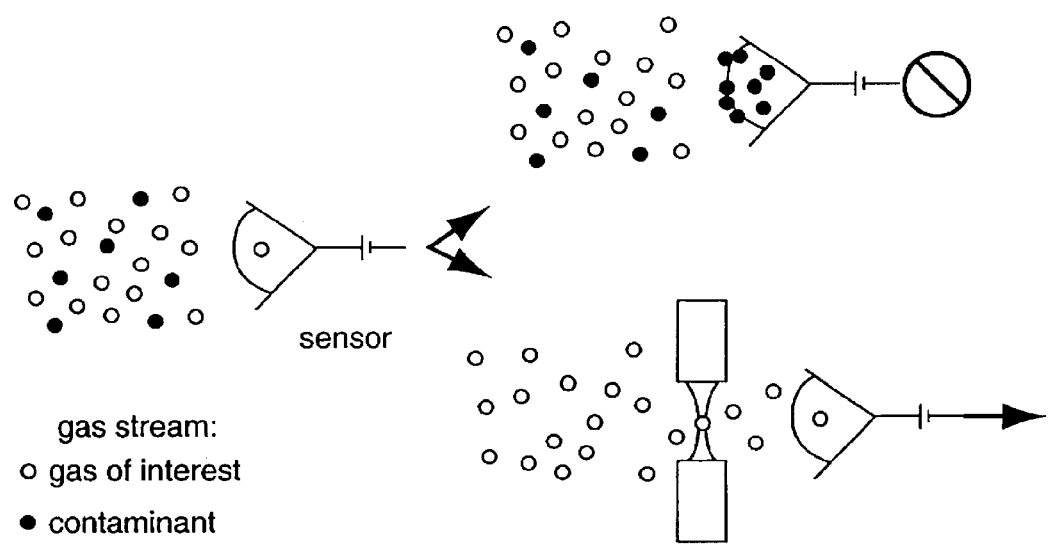
FIG. 5 shows operation of a meniscus-shaped membrane for selective separation in accordance with the present invention.

Applications for small, selective membranes that can be easily integrated into commercial devices are numerous. For example, in the growing field of sensors and control switches it is often crucial to avoid the contamination of the sensor itself with non-innocent matrix constituents (FIG. 5). For example, carbon monoxide sensors are available with excellent selectivity for CO but their susceptibility to contamination by volatile organic compounds often limits their commercial use. A pre-filter (polymer membrane) that permeates CO selectively and at high flux provides a significant improvement to sensor designs. Such a pre-filter can be applied in any detector having a sensing element responsive to the presence of a pre-selected species, where the sensing element is characterized as subject to deactivation or a reduction in activity in the presence of selected volatile organic materials. By location of such a polymer membrane between such a sensing element and any ambient atmosphere (the polymer membrane capable of allowing the pre-selected species to pass through to the sensing element while the polymer membrane prevents sufficient selected volatile organic materials to pass through to the sensing element), the sensing element can be protected from deactivation or a reduction in activity.

Figure 6:
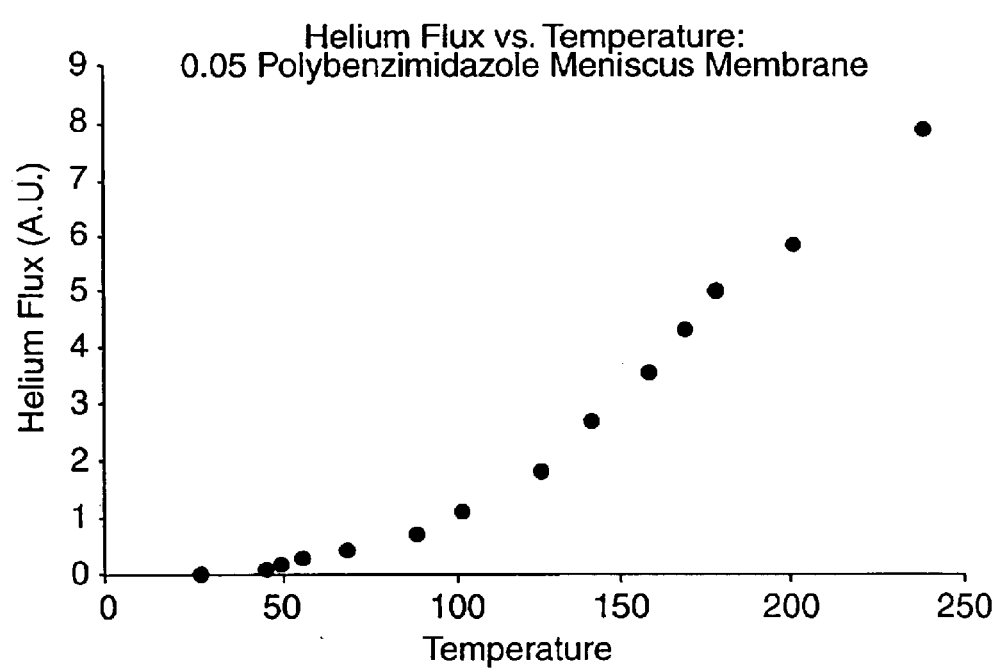
FIG. 6 shows a graph of temperature versus helium flux for a meniscus-shaped membrane of polybenzimidazole in accordance with the present invention.
Figure 7:
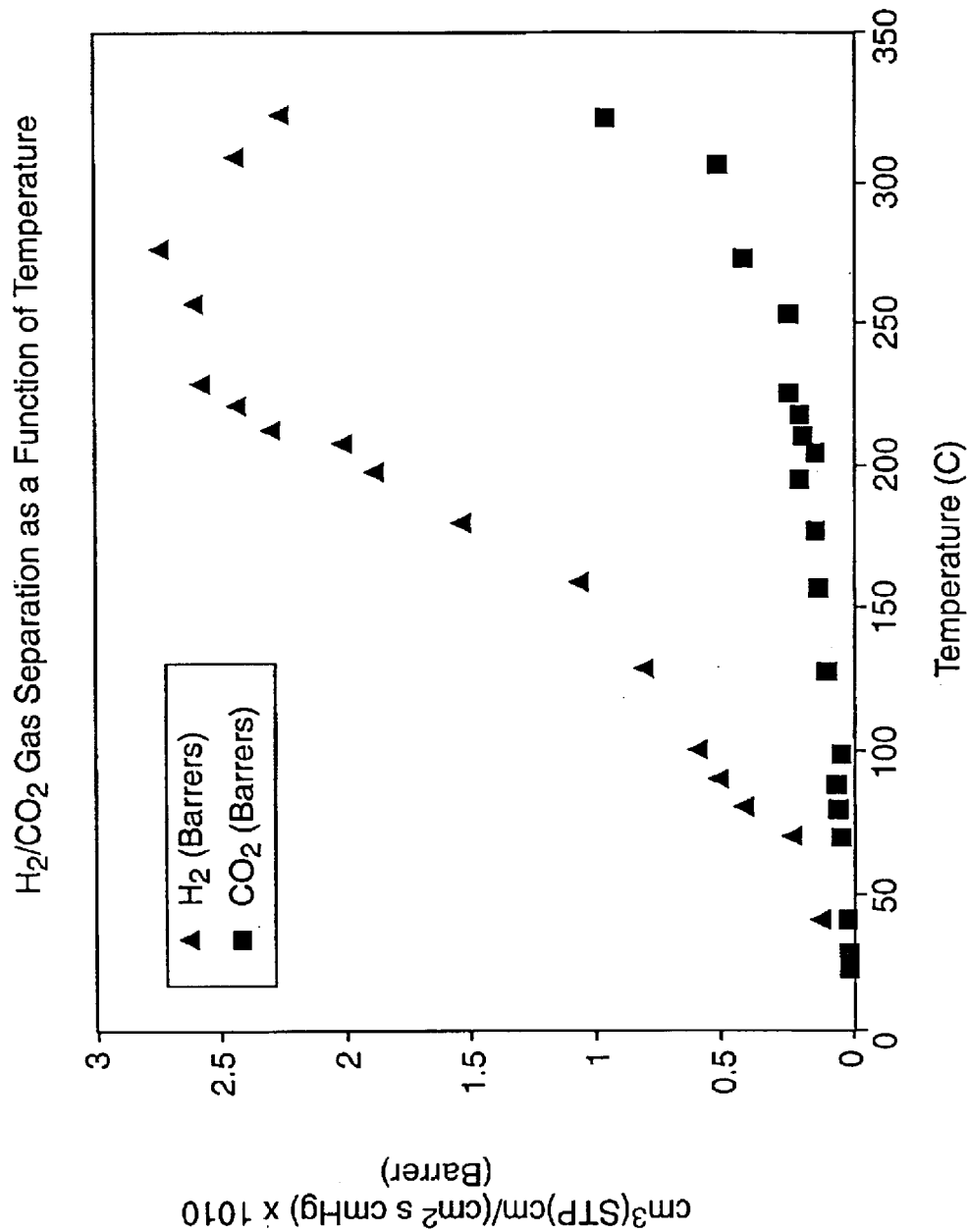
FIG. 7 shows a graph of temperature versus hydrogen flux and carbon dioxide flux for a meniscus-shaped membrane of polybenzimidazole in accordance with the present invention.
Figure 8:
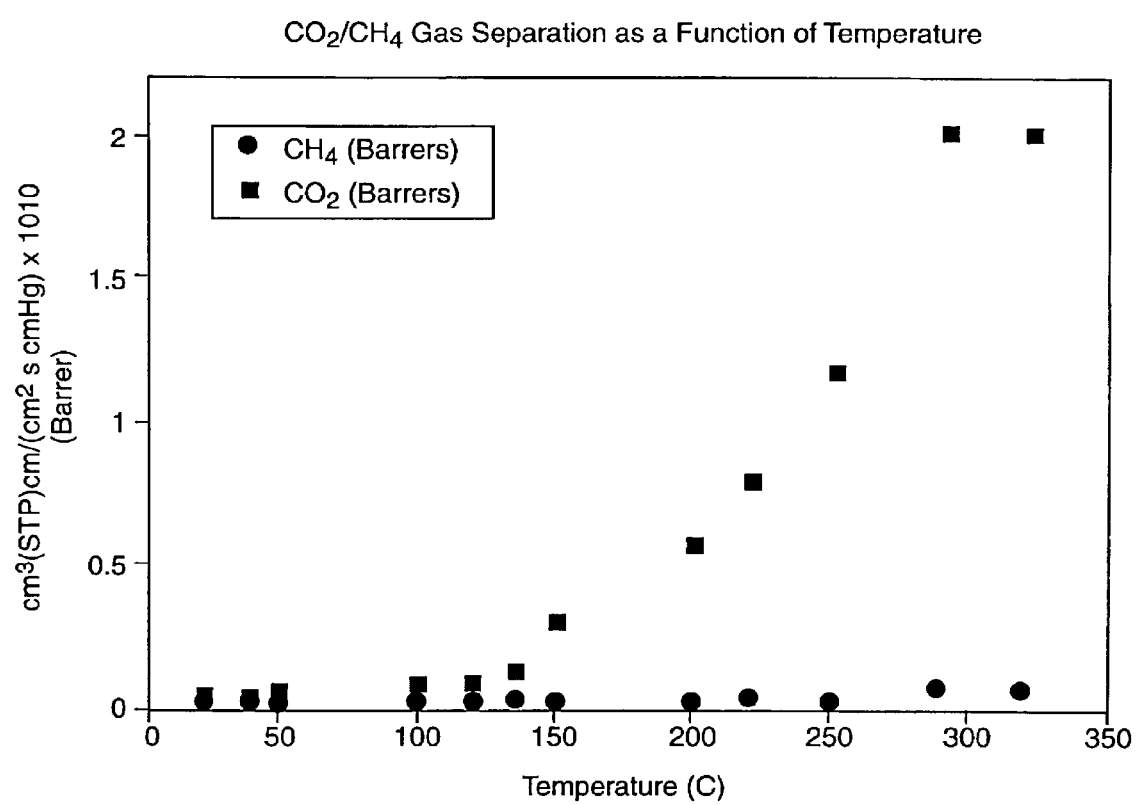
FIG. 8 shows a graph of temperature versus carbon dioxide flux and methane flux for a meniscus-shaped membrane of polybenzimidazole in accordance with the present invention.

Several properties of solid polymer membranes for gas separation also appear to have important potential for commercial application when in the meniscus form. The solubility selectivity of gases in polymer membranes can be changed by varying the backbone structure as well as the type and distribution of functional groups. Selectivity for certain gases can also be achieved by controlling the interchain spacing (i.e., free volume) in the matrix. Temperature can also be used to affect the separation performance of polymer membranes. As the temperature increases, thermal motion causes increased permeability of gases through the polymer. This behavior is shown in the graphs of FIG. 6, FIG. 7 and FIG. 8. Different gases (FIGS. 7 and 8) can have different flux rates at different temperatures yielding the opportunity for separation from one another.

Pressures of up to 100 psig have been withstood by the meniscus membranes of the present invention without failure, marking a significant improvement over the operating pressure of many freestanding polymer films. Advances in stability may be made with control of the hole geometry as well as the introduction of covalent interactions between the polymer and the metal support (silane coupling).

The gas separation performance of the meniscus-shaped membrane is highly dependent on the polymer structure. Preliminary data using PBI membranes in this configuration have shown that the performance is quite good and can be adjusted with temperature (FIG. 6).

Of particular interest are the following features of the meniscus membrane. The tunability of the gas separation performance is quite important for any application in which selectivity for a particular gas is desirable. The tradeoff between gas diffusivity and solubility in the polymer with the thickness of the membrane often makes optimization difficult in thin film membranes. Control over hole size as well as polymer loading (i.e., membrane thickness) and polymer structure (backbone structure, extent of crosslinking, functionalization with gas solubility functionality, and the formation if interpenetrating polymer networks) can give a valuable element of control in forming selective membranes for low flux applications (sensors).

The ability to form gas tight polymer films with high reproducibility that can be readily tested is seen as an important contribution to membrane gas separation technology. This invention allows the rapid screening of membranes consisting of different polymers in a variety of thicknesses.

The solid polymer membranes of the present invention can generally be formed of any solid polymer material capable of forming a meniscus-shaped membrane within a pore or opening of a substrate. Generally, glassy polymers are preferred. High gas separation factor materials are frequently glassy polymers. Representative examples of such polymers include polyesters, polyestercarbonates, sulfonated polysulfones and sulfonated poly(phenylene oxides), cellulosic derivative polymers, such as cellulose acetate or blends of cellulose acetate with poly(methyl methacrylate) to name a few. Also, the solid polymer material should be stable, both chemically and physically at high temperatures of above about 150° C.

The permeability of a gas or vapor through a membrane is a product of the diffusion coefficient, D, and the Henry's law sorption coefficient, k. D is a measure of the permeate's mobility in the polymer; k is a measure of the permeate's sorption into the polymer. The diffusion coefficient tends to decrease as the molecular size of the permeate increases, because large molecules interact with more segments of the polymer chains and are thus less mobile. The sorption coefficient depends, amongst other factors, on the condensability of the gas.

Depending on the nature of the polymer, either the diffusion or the sorption component of the permeability may dominate. In rigid, glassy polymer materials, the diffusion coefficient tends to be the controlling factor and the ability of molecules to permeate is very size dependent. As a result, glassy membranes tend to permeate small, low-boiling molecules, such as hydrogen and methane, faster than larger, more condensable molecules, such as $C_2+$ organic molecules. For rubbery or elastomeric polymers, the difference in size is much less critical, because the polymer chains can be flexed, and sorption effects generally dominate the permeability. Elastomeric materials, therefore, tend to permeate large, condensable molecules faster than small, low-boiling molecules.

Among the suitable solid polymer materials are included cellulose acetates, polyimides, polystyrenes, poly (alkyl methacrylate)s and copolymers of poly (alkyl methacrylate)s and other acrylates or blends thereof where alkyl can be methyl, ethyl and the like, poly(vinyl chloride)s, polysulfones, and polybenzimidazoles. Preferably, the solid polymer material is a polybenzimidazole that is thermally stable up to temperatures of at least about 450° C.

The solid polymer membranes of the present invention can also include semi-interpenetrating polymer networks such as blends of Thermid FA-700 thermosetting polyimide (commercially available from the National Starch and Chemical Corporation) and a thermoplastic polyimide heat treated at 250° C. to alter the polymer rigidity and inhibit interchain mobility so as to enhance control of diffusion pathways.

In one embodiment, the solid polymer membranes of the present invention may also surface functionalization, e.g., with $CO_2$-philic groups (such as amines, sulfolenes, sulfolanes and carboxylates) so as to enhance selectivity of the solid polymer membranes for carbon dioxide.

The meniscus membranes of the present invention may be used as a thermal gas switch in a temperature valve approach. That is, a meniscus membrane may be positioned at a place within a system at which a particular gas is retained behind the meniscus membrane until the meniscus membrane reaches a selected temperature whereat the membrane allows the particular gas to pass through at some measurable flux. Thus, a thermal gas switch or temperature Valve is provided. Thus, at a first selected temperature the pre-selected gas can be retained while at a second selected temperature the pre-selected gas can pass. The first and second pre-selected temperatures are generally about 25° C. apart, preferably about 10° C. apart, more preferably as little as about 1° C. apart.

As a pre-concentration approach, the meniscus membranes of the present invention may be used for a mass spectrometry interface such that a semi-selective membrane may be used as the initial aperture of the machine.

The meniscus membrane design of the present invention would be valuable in fixtures ranging from thermal gas switches and flow controllers to gas purifiers in confined settings (such as, e.g., hydrogen gettering).

The present invention is more particularly described in the following example, which is intended as illustrative only, since numerous modifications and variations will be apparent to those skilled in the art.

EXAMPLE 1

A polybenzimidazole (PBI) meniscus-shaped membrane formed in an opening of size (0.005 inch) was exposed to a helium feed stream. At room temperature the permeance was negligible, but as the temperature was raised the flux increased significantly as shown in FIG. 6. Given the correct combination of selectivity and flux, selective separation of particular gas components may be achieved.

The formation of a leak tight (helium) seal between the metal edge and the polymer membrane. The holes range in size form 0.03 to 0.1 inches in diameter (drilled through a ¾ inch stainless steel disk, 0.0275 inch in thickness).

Additional data from polybenzimidazole (PBI) meniscus-shaped membrane formed in various openings is shown in Table 1.

Gas Separation Data fron PBI Meniscus Membranes

| Temp. (° C.) | Single Gas Performance $cm^3(STP)cm/(cm^2\ s\ cmHg) \times 10^{10}$ (Barrer) | | | Ideal Gas Separation | | Mixed Gas Separation Factor | |
|---|---|---|---|---|---|---|---|
| | He | $H_2$ | $CO_2$ | $He/H_2$ | $H_2/CO_2$ | $H_2/CO_2$ | $CO_2/CH_4$ |
| 25  | 0.03 | 0.009 | 0.007 | 3.3 | 1.3 | 1.9 | — |
| 50  | 0.19 | 0.09  | 0.05  | 2.1 | 1.8 | 5.1 | 6.3 |
| 100 | 0.84 | 0.74  | 0.30  | 1.1 | 2.5 | 9.9 | 7.8 |
| 150 | 4.46 | 3.91  | 1.99  | 1.1 | 2.0 | 8.0 | 23.1 |
| 200 | 8.11 | 9.54  | 4.26  | 0.9 | 2.2 | 9.1 | 25.5 |
| 250 | 17.3 | 18.9  | 8.56  | 0.9 | 2.2 | 10.5 | 50.5 |

The process of the present invention should help overcome major economic and environmental challenges to gas separations.

Although the present invention has been described with reference to specific details, it is not intended that such details should be regarded as limitations upon the scope of the invention, except as and to the extent that they are included in the accompanying claims.

What is claimed is:

1. A temperature gas valve comprising a gas separation module including a substrate containing at least one opening therein and a polymer material contained within the opening of said substrate, said polymer material characterized as forming a meniscus-shaped separator within said opening, said temperature gas valve characterized as preventing a pre-selected gas to pass through said polymer material at a first temperature, but allowing said pre-selected gas to pass through said polymer material at a second temperature.

2. The temperature gas valve of claim 1 wherein said first temperature and said second temperature are at least 1° C. apart.

* * * * *